(12) United States Patent
Aslund

(10) Patent No.: US 7,496,176 B2
(45) Date of Patent: Feb. 24, 2009

(54) METHOD AND ARRANGEMENT RELATING TO X-RAY IMAGING

(75) Inventor: Magnus Aslund, Stockholm (SE)

(73) Assignee: Sectra Mamea, Kista (SE)

( * ) Notice: Subject to any disclaimer, the term of this patent is extended or adjusted under 35 U.S.C. 154(b) by 27 days.

(21) Appl. No.: 10/597,965

(22) PCT Filed: Feb. 14, 2005

(86) PCT No.: PCT/SE2005/000194

§ 371 (c)(1),
(2), (4) Date: Aug. 14, 2006

(87) PCT Pub. No.: WO2005/077277

PCT Pub. Date: Aug. 25, 2005

(65) Prior Publication Data

US 2007/0165781 A1 Jul. 19, 2007

(30) Foreign Application Priority Data

Feb. 13, 2004 (SE) .................................. 0400347

(51) Int. Cl.
*H05G 1/38* (2006.01)

(52) U.S. Cl. .............................. 378/96; 378/97; 378/37

(58) Field of Classification Search .................. 378/37, 378/39, 97, 16, 96, 108–112, 146
See application file for complete search history.

(56) References Cited

U.S. PATENT DOCUMENTS

| 4,032,784 | A | 6/1977 | Rich |
| 4,942,596 | A | 7/1990 | Eberhard |
| 4,972,458 | A | 11/1990 | Plewes |
| 5,585,638 | A | 12/1996 | Hoffman |
| 6,873,682 | B2 * | 3/2005 | Francke et al. ................. 378/97 |
| 2003/0174806 | A1 | 9/2003 | Francke et al. |
| 2004/0141588 | A1 * | 7/2004 | Francke et al. .............. 378/146 |
| 2004/0157853 | A1 | 8/2004 | Bonnert |

* cited by examiner

*Primary Examiner*—Hoon Song
(74) *Attorney, Agent, or Firm*—Fox Rothschild LLP

(57) ABSTRACT

The present invention relates to a method and arrangement for controlling exposure in an e-ray apparatus, for depicting an object. The apparatus comprises an x-ray source and a displaceable detector being arranged to move with a controllable speed across an image exposure area. The method comprises the step of: acquiring a signal relating to photons incident on at least a part of the detector, comparing said acquired signal with a target value, and controlling the speed of detector, displacement with respect to the result of the comparison.

24 Claims, 6 Drawing Sheets

METHOD AND ARRANGEMENT RELATING TO X-RAY IMAGING

CROSS REFERENCE TO RELATED APPLICATIONS

This application claims priority benefit under 35 U.S.C. §365(a) of International Patent Application No. PCT/SE05/000194 filed 14 Feb. 2005, which, in turn, claims priority benefit of Swedish Patent Application Serial No. 0400347-1 filed Feb. 13, 2004. The entire contents of both applications are hereby incorporated in total by reference.

THE FIELD OF THE INVENTION

The present invention relates to a method and arrangement for Automatic Exposure Control (AEC) in an X-ray apparatus.

THE BACKGROUND OF THE INVENTION

AEC is a mode of operation of an X-ray machine by which the x-ray output is automatically controlled and terminated when a pre-set radiation exposure to the image receptor is reached. It may also operate in such a way that a pre-exposure is made before the diagnostic exposure and a sensor, e.g. part of the sensor used for the diagnostic imaging, is measuring the outcome of the pre-exposure and from the measured data the optimum parameters for the diagnostic exposure is calculated. The parameters that can be optimised for a diagnostic exposure are typically x-ray tube potential (kV), x-ray tube current (mA), x-ray exposure time, x-ray filter material, and x-ray anode target material may also be automatically selected.

The function of the AEC is to assure that the image is exposed correctly, independent of the object. A correct exposure implies that the image receives sufficient statistics. The level of statistics in an image is proportional to the tube current (mA) and the exposure time (s). Thus, the tube loading (mAs) is a quantity used to describe the exposure.

The optical density control of a film system is essential in order to expose modern high-sensitive films correctly. A digital system, e.g. for mammography, could similarly struggle to obtain a certain signal to noise ratio (SNR) in the image for different breast types and entrance spectrum.

There are a number of ways to implement an AEC. The patent documentation describes some, e.g.:

U.S. Pat. No. 4,357,708 relates to an arrangement to the path of movement of the photographic exposure unit comprised of an x-ray tube and image layer (or film) carrier can be selected. For determination of the photographic exposure time, either a mAs-relay or an automatic exposure timer with a radiation detector may be placed in control of the energization of the x-ray tube. The x-ray tube current or the current of the radiation detector are integrated and the integrator contents are sampled at a predetermined time following commencement of the photographic exposure. The sampled value is compared with a reference value and the running speed of the photographic exposure unit is influenced in such a fashion that the photographic exposure time determined by the switching of the mAs-relay or by the automatic exposure timer approximately corresponds to the running time of the photographic exposure unit.

In U.S. Pat. No. 4,383,327 a scanning radiographic system employing a multi-linear array is disclosed. The system includes a source of electronic radiation, which is incident upon the multi-linear array. The multi-linear array includes radiation sensors each of which is adapted to generate an intensity signal as a function of the amount of radiation sensed thereby. Each sensor has associated therewith a means for holding or storing its respective intensity signals. The intensity signals thus held may be continually up-dated to reflect subsequent intensity signals resulting from additional radiation sensed by the respective sensors. An opaque object to be scanned by the radiographic system passes through the beam of radiation in a controlled fashion. This controlled motion is synchronized and coordinated with the shifting of the up-dated intensity signals so that the speed and course of travel of a particular up-dated intensity signal through the holding means of a given group of said sensors is optically aligned with the speed and course of travel of the radiation passing through a given area of the opaque specimen. In this fashion, there is generated one up-dated intensity signal corresponding to a given area of the opaque specimen. These up-dated intensity signals are then collected and processed by a suitable visual system.

WO 03/043497 relates to automatic exposure control implemented in imaging by electromagnetic radiation, in particular to automatic exposure control in film-based mammography, which is based on a completely new approach as compared with the solutions currently in use, which utilize adjustment curves and/or tables constructed on the basis of empiric tests. The new approach includes modelling into the AEC system the radiation spectra obtainable from the radiation source as a function of its operating parameters and attenuation of the spectrum as the radiation traverses components of the imaging apparatus. By measuring the thickness of the object to be imaged and knowing the initial spectrum and its calculable behaviour, a correspondence between the AEC signal and the desired darkening of the image can be achieved which is based on true density of the object being imaged.

Other papers include "A scanning system for chest radiography with regional exposure control: theoretical considerations", Plewes D B, Med Phys. 1983 September-October; 10(5): 646-54. According to this document, the presence of scattered radiation and the small useful exposure range of radiographic film limit conventional chest radiography. A computer-assisted scanning system to minimize these two effects is outlined. The system uses a small beam of radiation swept over the patient's chest in a raster pattern to expose a conventional film cassette, while a slit collimator scanning between the patient and the film serves to reject scattered photons. A microcomputer measures beam attenuation by the patient with a detector placed behind the film, which in turn automatically adjusts the x-ray tube output to minimize excursions in film exposure as the beam scans. A formalism, which relates the patient transmission and film exposure distribution, is developed and a system transfer function is given. It is shown that such a system operates as a spatial filter, which attenuates film contrast for structures of spatial frequency less than the inverse scanning beam width. By manipulating the software parameters of the feedback network, it is possible to alter this filter and produce radiographs with low spatial frequency enhancement, attenuation, or contrast inversion.

US 2003/0174806 relates to an apparatus for recording a two-dimensional image of an object. The apparatus comprises a plurality of one-dimensional detector units, each exposed to ionizing radiation transmitted through or scattered off the object, which is arranged for one-dimensional imaging of the radiation. The apparatus includes a device for moving the detector units relative the object while the detector units repeatedly detect to create the two-dimensional image of the object and a control device for controlling the detector units to detect ionizing radiation during a short period of time before or during an initial part of the movement, calculating an optimum exposure time for the repeated detection based on the short period of time detection, and controlling the repeated detection to automatically obtain the optimum exposure time.

According to this document, a pre-scan is performed before conducting a examination scan. The pre-scan values are used to adjust the examination scan parameters, such as scan speed.

In U.S. Pat. No. 5,585,638 an x-ray detector for an automatic exposure control system is disclosed. The apparatus has a substrate of carbon composite material with a first layer of conductive material on a major surface of the substrate and a second layer of homogeneous semiconductive material is deposited on the first layer and has an electrical characteristic, such as conductivity, that varies in response to impingement of x-rays. A third layer of conductive material is formed on the surface of the semiconductor layer and is divided into a plurality of electrode elements which define a plurality of regions in the layer of semiconductive material. By sensing the conductivity between the first layer and each of the electrode elements, the intensity of x-rays striking the different regions can be measured. Thus, a scintillator is used to convert protons to photons.

The detector according to this invention converts protons to photons and then to electrical signals. However, the system does not use photon counting, i.e. the number of the photons incident to a detector.

THE SUMMARY OF THE INVENTION

A problem with state-of-the art mammography systems and corresponding AECs is that the exposure is not optimised in every area of the image, the systems can only deliver and average exposure that will be too high in thin areas of the breast and in fatty areas of the breast with low attenuation of the x-rays while it will be to high in dense areas of the breast with predominantly glandular tissue that is more opaque to x-rays. The current invention solves this problem since the pre-exposure is combined with the diagnostic exposure in a real-time system and the exposure needs only to be averaged in one dimension (orthogonal to the scan direction) while it may be fully optimised in the other dimension (the scan direction). Thus a significantly improved exposure over the breast can be achieved.

Problems related to scanning systems are to obtain precise and stable mechanical motion over time and wear of the mechanical parts. If the position of the scanning detector is accurately measured under all conditions, something that is relatively easy to achieve, and the system is read out at triggers from the measurement of the position, e.g. every 50 µm, and the time between triggers is measured accurately with an external clock, the measured exposure at the detector can be normalized in such a way that the system becomes insensitive to mechanical instability; thus, a very robust system is achieved. Input to AEC will be the normalised signal from a detector, i.e. the signal per true 50 µm, the time the exposure was collected measured with the external clock. The time will be used to calculate actual velocity 50 µm/t and also non-normalise the detector signal.

Conventional film based systems or systems based on computed radiography measure the exit kerma in some discrete number of regions under the breast and terminate the exposure based on the exposure in these regions. Digital systems with area detectors usually do a pre-exposure to determine the density of the breast and thus provide input to the AEC.

The proposed method scans the object (breast) with the detector that controls the exposure time. Conventional systems have the same exposure time for each point of the breast. The method according to the invention controls the exposure of each point based on the signal or density in the very same point, at least in the scan direction. Conventional film based systems control the exposure time by terminating the exposure. The proposed system may control the exposure in real time during the acquisition by altering any of scan speed, tube current (mA), tube voltage (kV), anode material and filter. According to the preferred embodiment of the invention, the system controls the exposure time by varying the scan-speed and thus the exposure time of each point in the scanning direction. The scanning speed is based on the exposure substantially in the every point being exposed.

Thus, the object of the present invention according to preferred embodiments of the invention is to provide a novel method and arrangement for Automatic Exposure Control, which lacks the drawbacks of the prior art. The invention beside conventional x-ray imaging systems is also suitable for X-ray diagnostic apparatus using photon-counting technique. This invention is particularly suitable for photon counting detectors, since there is a simple relationship between counted photons and SNR. Also the detector is very linear which further means a simple relationship to scan speed and target signal. Preferably, the object of the present invention is to provide a system based on a non-constant scan-velocity, which is controlled in substantially real-time during the scan.

Thus, to solve aforementioned problems and achieve the objectives of the invention a method of controlling exposure in an x-ray apparatus, for depicting an object is provided. The apparatus comprising an x-ray source, a displaceable detector, being arranged to move with a controllable speed across an image exposure area. The method comprises the steps of: acquiring a signal relating to photons incident on at least a part of the detector, comparing said acquired signal with a target value, and controlling the speed of detector displacement with respect to the result of the comparison. The target value is calculated from object thickness and spectrum incident on the object. Preferably, the signal is acquired from a discrete number of regions on said detector. Most preferably, the detector is a photon-counting detector and the signal is the counted number of photons. The target signal is calculated to obtain a pre-defined signal to noise ratio (SNR).

Preferably, a distance the detector moves between readouts defines pixels in the scan direction, first dimension, and in a second dimension, the detector comprises actual pixels. The detector functions as an exposure control as well as an image receptor. According to one embodiment, based on the number of photons collected in a predefined region of the detector the scan velocity is modified.

Preferably, scan-speed is changed with respect to a count rate change in said region for controlling the number of counts reached per a first dimension pixel. A feedback from the displaceable detector based on the count rate in said region.

Most preferably, the feedback is substantially real-time and controls the scan speed of the detector.

In one embodiment, the exposure of each point along an x-axis is controlled based on the count rate of the said region and thus the entire image has a controllable signal level along the first dimension at least in said region in the second dimension. The method further comprises minimizing total scan time by areas not covered by dense objects being scanned faster and thus exposed shorter. Preferably, the detector itself is used to control the exposure.

The invention also relates to a method of controlling exposure time in an x-ray apparatus, the method comprising the steps of: setting a target signal, setting a detector Region Of Interest (ROI), setting a start velocity, start scanning, collecting a signal from said ROI, compensating the signal with respect to at least one of ROI size and efficiency, comparing the signal with a target signal ($S_{target}$) and calculating a new optimal velocity, and setting a new velocity.

The method further comprises reading a number of photons counted or SNR. Most preferably, the x-ray apparatus is a photon counting device and the new velocity ($V_{new}$) is calculated as $V_{new}=V_{old} \times S_{target}/S_{measured}$.

The method further comprises: if target signal is higher than measured signal then velocity is decreased otherwise old velocity is kept. The method further includes requiring new velocity to be at least higher than a pre-set minimum velocity. Depending on the detector size the velocity may decrease if the target signal is higher than the measured signal otherwise the velocity is increased.

Alternatively, the method comprises: collecting a compression height data, projection and data about an examination type, collecting from previous examinations, based on previous step, typical examination object density profile, calculating an optimal velocity profile based on estimation of said density profile and measured signals, and calculating new velocity based on the above data The method for choosing the ROI includes: deciding a scan direction, choosing ROI that will enter the object first, and checking that ROI has sufficient number of detector elements working else choosing next appropriate ROI.

The invention also refers to an arrangement for controlling exposure time in an x-ray apparatus, which comprises an x-ray source and a displaceable detector being arranged to be displaced with a controllable speed across an image exposure area. The arrangement comprises means for receiving detected signals by said detector, including a comparator unit for comparing said acquired signal with a target value, and means for controlling the speed of said detector displacement with respect to the result of the comparison. The means for receiving detected signals is a processing unit and said means for controlling the detector replacement is a motor controller. The displacement controller controls rotation of said detector having a rotation centre in said x-ray source.

The invention also relates to an X-ray apparatus of a photon counting type, comprising an x-ray source and a displaceable detector being arranged to move with a controllable speed across an image exposure area. The apparatus comprises an arrangement for counting the number of photons detected by the detector, means for comparing the counted number of photons with a pre-set value, and means for controlling the speed of detector displacement with respect to a result obtained from the density of an object to be examined.

Moreover, the invention relates to a computer useable medium having computer readable program code embodied therein to enable controlling exposure in an x-ray apparatus, when imaging an object, the apparatus comprising an x-ray source and a displaceable detector. The computer program code is arranged to control displacement of said detector array with a controllable speed across an image exposure area. The computer program code comprises: an instruction set for acquiring a signal relating to photons incident on at least a part of the detector, an instruction set for comparing said acquired signal with a target value, and instruction set for controlling the speed of detector displacement with respect to the result of the comparison. A computer program for controlling exposure in an x-ray apparatus is also given, when imaging an object, the apparatus comprising an x-ray source, a displaceable detector. The computer program is arranged to control displacement of said detector array with a controllable speed across an image exposure area. The computer program comprises: an instruction set for acquiring a signal relating to photons incident on at least a part of the detector, an instruction set for comparing said acquired signal with a target value, and instruction set for controlling the speed of detector displacement with respect to the result of the comparison.

According to one aspect a computer useable medium having computer readable program code embodied therein is provided to enable controlling exposure in an x-ray apparatus for imagining an object. The apparatus comprises an x-ray source and a displaceable detector being arranged to move with a controllable speed across an image exposure area. The code comprises: a first instruction set for acquiring a signal relating to photons incident on at least a part of the detector, a second instruction set for comparing said acquired signal with a target value, and a third instruction set for controlling the speed of detector displacement with respect to the result of the comparison. A computer program for controlling exposure in an x-ray apparatus, for imagining an object is given. The apparatus comprises an x-ray source and a displaceable detector being arranged to move with a controllable speed across an image exposure area. The program comprises: a first instruction set for acquiring a signal relating to photons incident on at least a part of the detector, a second instruction set for comparing said acquired signal with a target value, and a third instruction set for controlling the speed of detector displacement with respect to the result of the comparison.

SHORT DESCRIPTION OF THE DRAWINGS

In the following, the invention will be described in a non-limiting way with reference to a number of preferred embodiments illustrated schematically in attached drawings, in which.

Figure 8:
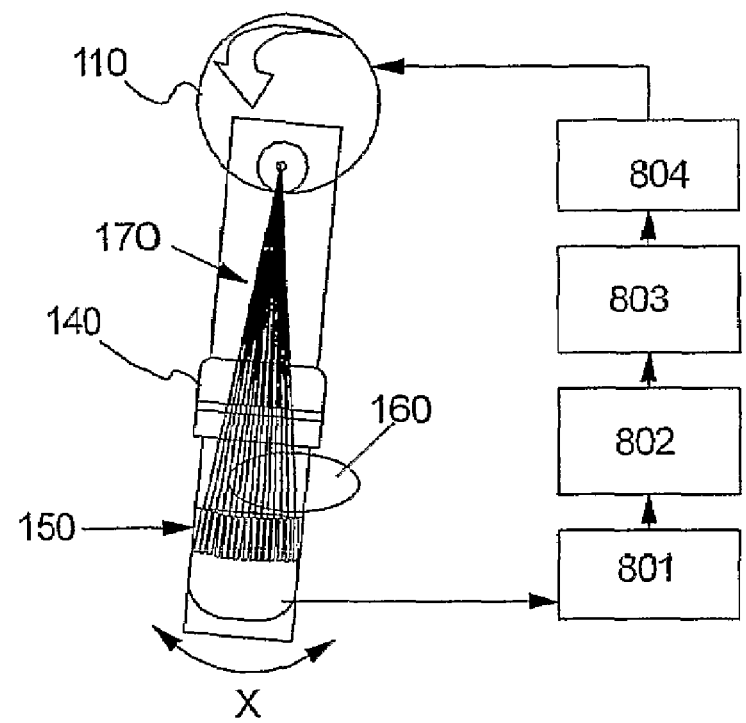
Figure 4:
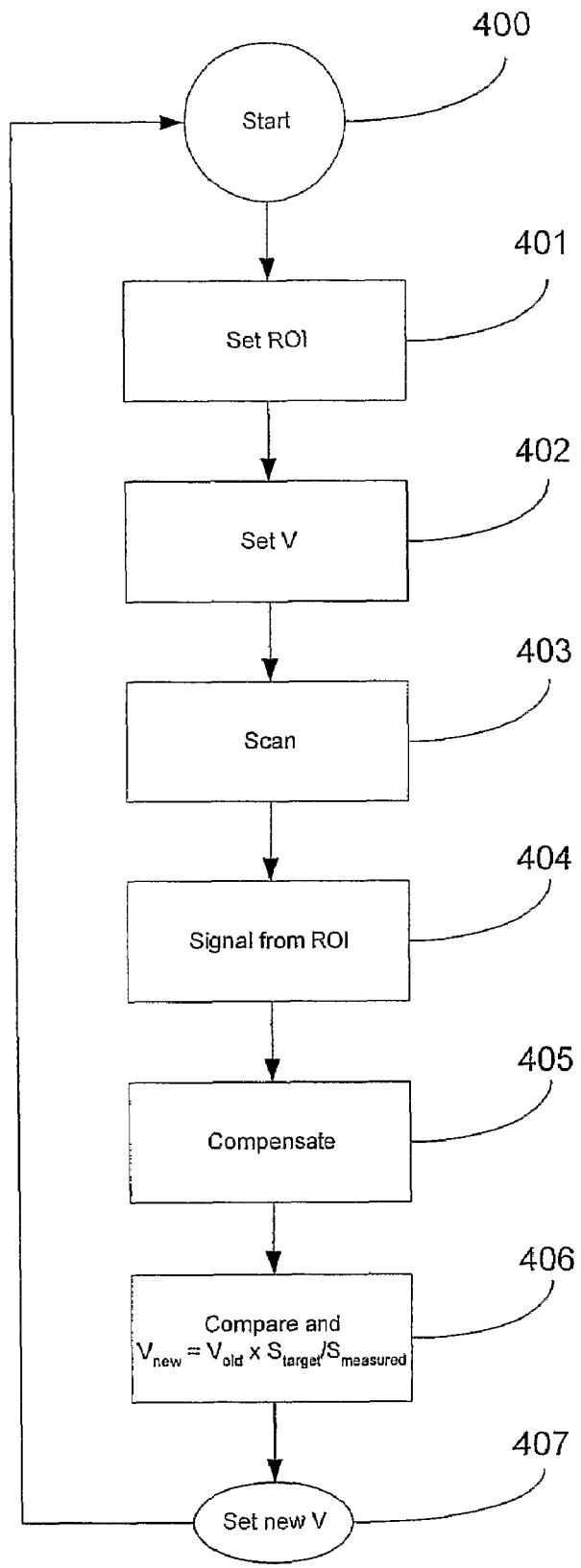
Figure 5:
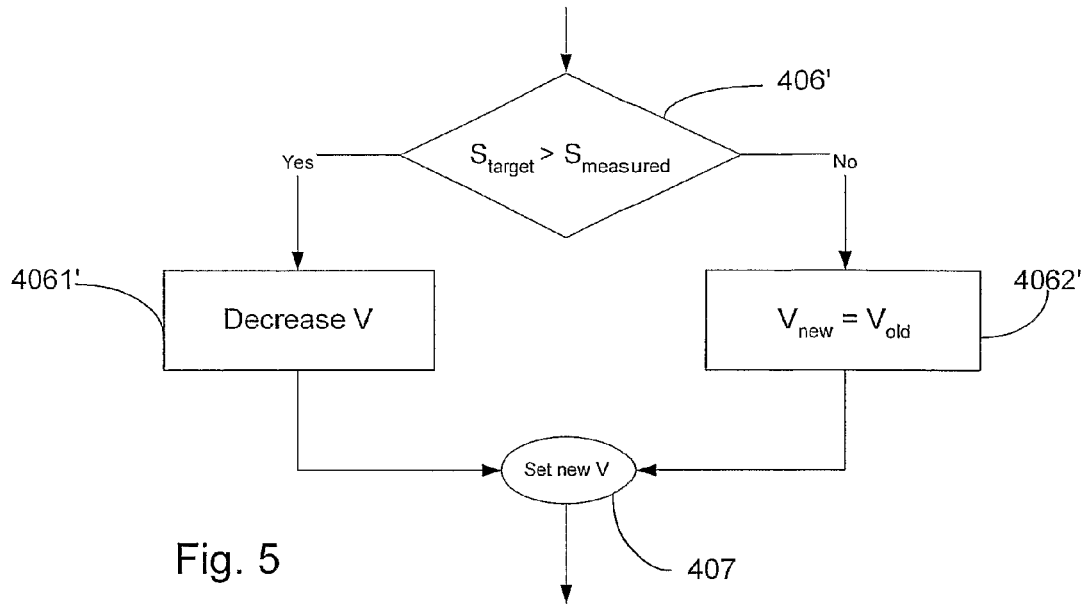
Figure 6:
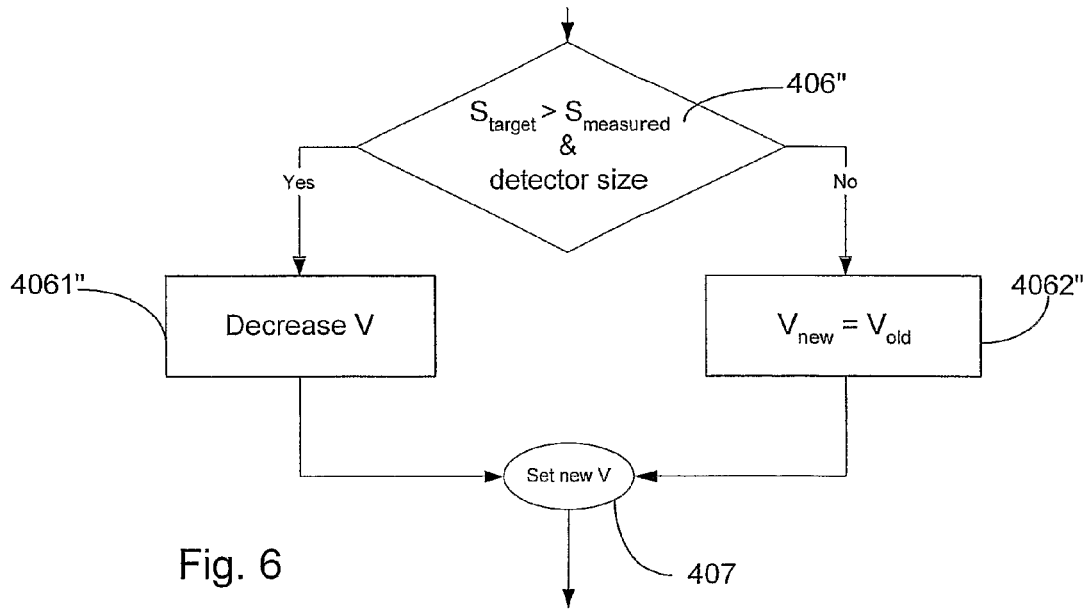
Figure 7:
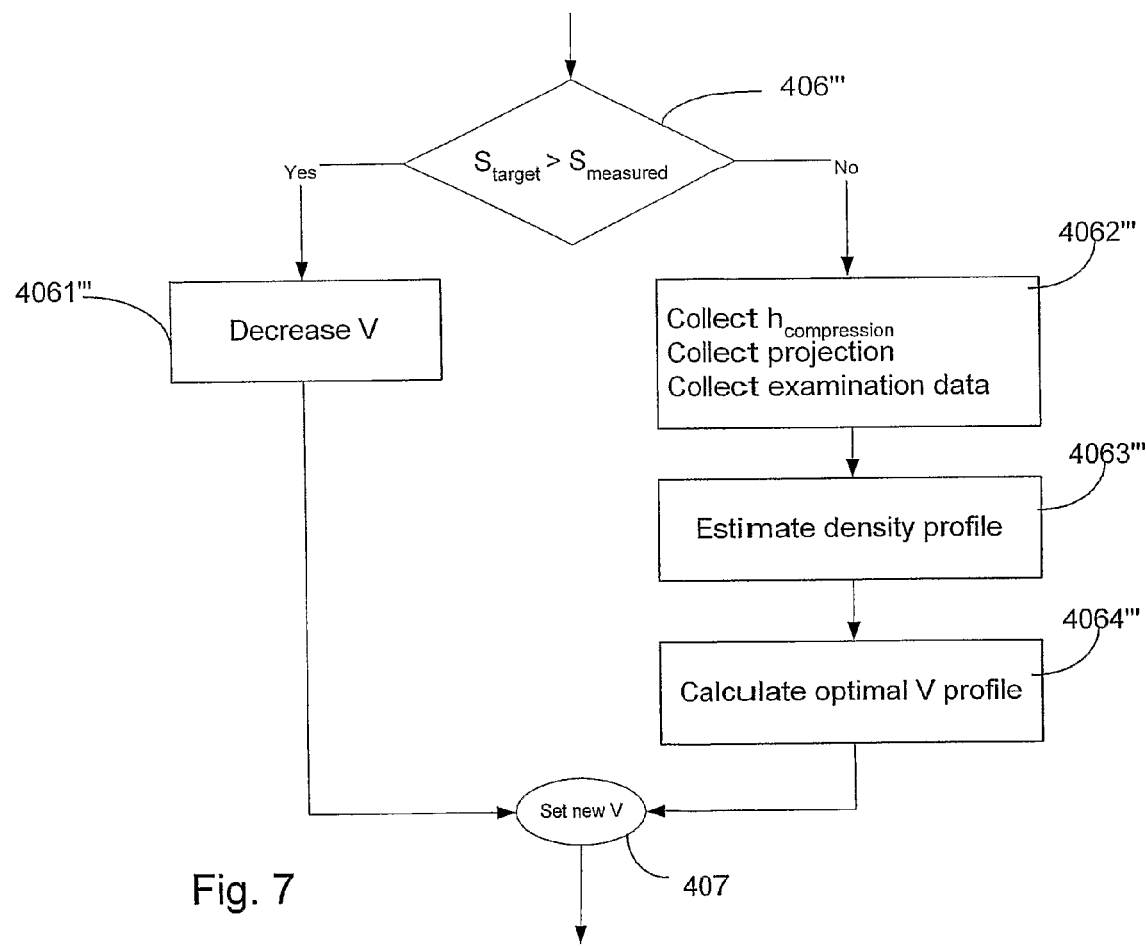

FIG. 4 is a flow diagram illustrating the steps according to one embodiment of the invention, FIG. 5 is a flow diagram illustrating an alternative step according to one embodiment of the invention, FIG. 6 is a flow diagram illustrating yet another alternative step according to one embodiment of the invention, FIG. 7 is a flow diagram illustrating yet another alternative step according to one embodiment of the invention, and FIG. 8 is a block diagram of the X-ray apparatus according to the invention.

DETAILED DESCRIPTION OF THE PREFERRED EMBODIMENTS

Figure 1:
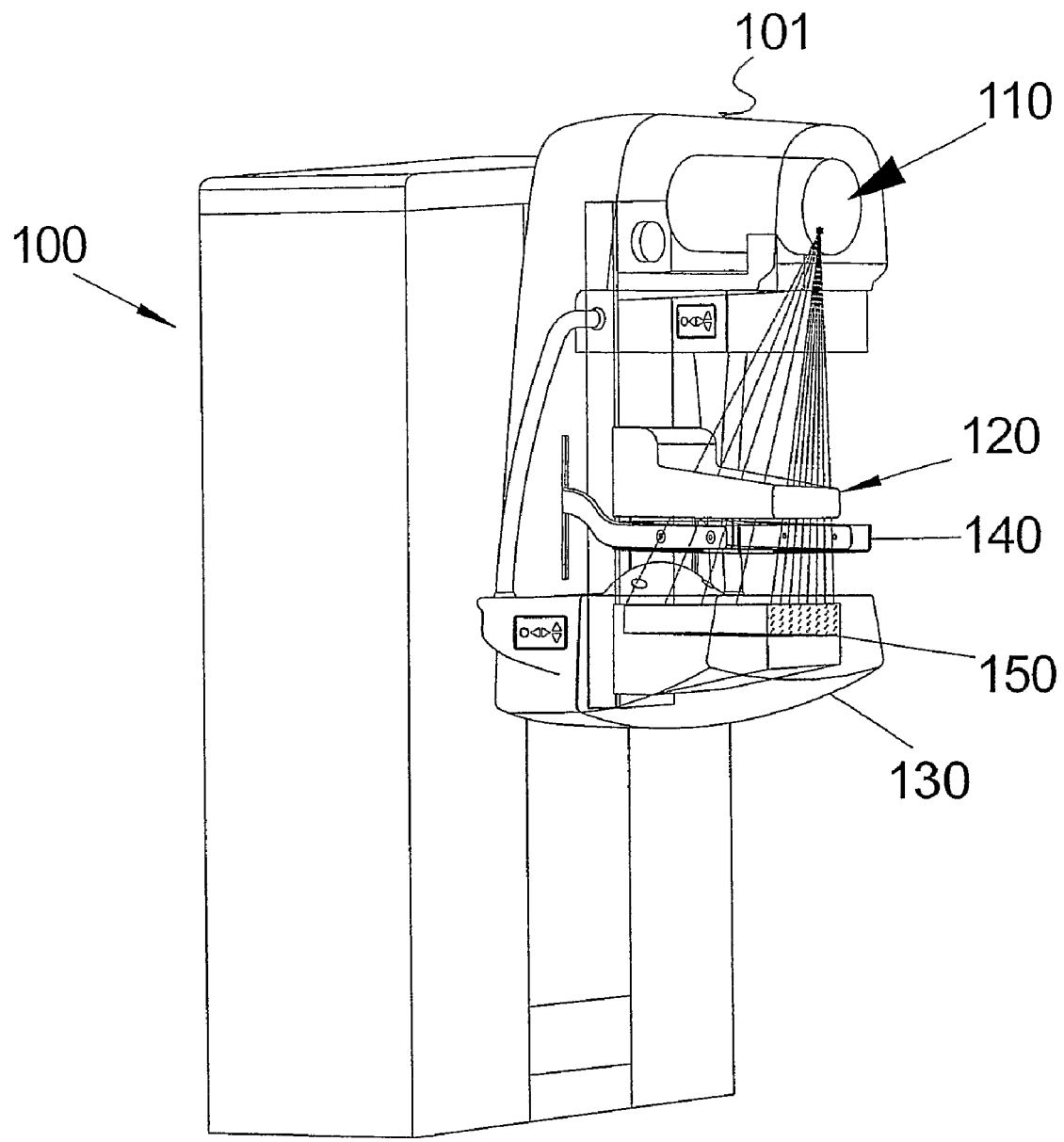
FIG. 1 is a schematic X-ray imaging apparatus in perspective.

FIG. 1 illustrates an X-ray imaging system 100, according to one preferred embodiment, based on a photon-counting detector that scans the image field in one dimension that is referred to as the x-dimension. The system 100 comprises an X-ray source (tube) 110 arranged in a housing 101, patient support 130 and pre-collimator housing 120 and compression paddle. A collimator 140 is arranged in a collimator support structure and the patient support 130 includes an array of detectors 150.

Figure 2:
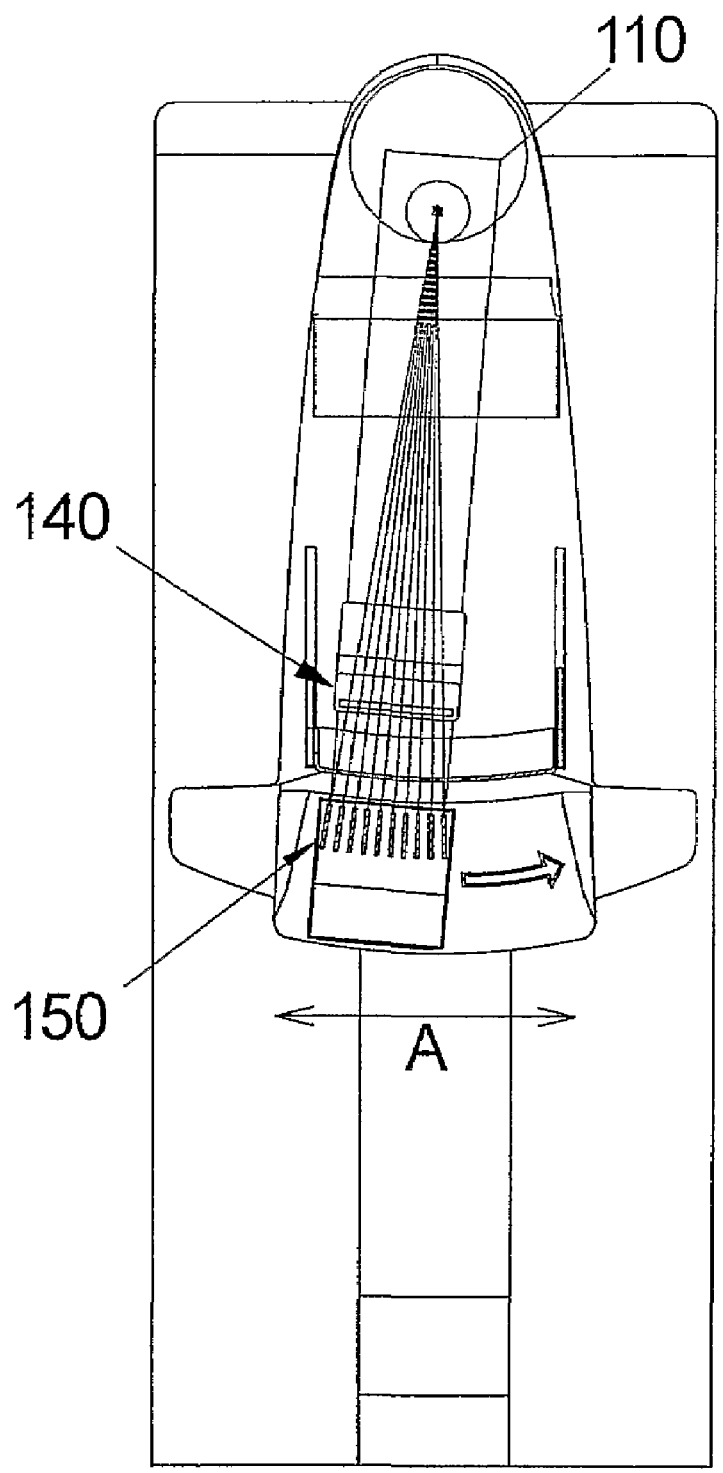
FIG. 2 is a schematic frontal view of the X-ray apparatus according to FIG. 1.

As it is illustrated in FIG. 2, the X-ray source 110 and detector array 150 are arranged to be displaced radially with the source 110 in the centre, thus scanning the section A. An image is acquired by scanning a detector across the image field. Whenever the detector has scanned a predefined distance, the number of photon counts collected is read-out and the counter is reset (zeroed). This means that the distance the detector moves between readouts defines the pixels in the scan direction. In the other dimension, the detector comprises actual pixels.

The detector covers the entire image field in y-dimension. In the y-dimension the detector comprises pixels. In the x-dimension, the system stores the number of counts collected during the time the detector moves a predefined length. This length is the size of the image's x-dimension pixels whereas the actual y-dimension pixels of the detector constitute the image's y-dimension pixels The number of photons per pixel needed to obtain a predefined Signal to Noise Ratio (SNR) is a function of kV, photon energy distribution and photon flux incident on the detector, but also the transit time per pixel in the x-dimension. The scanning image receptor will function as an exposure control as well as an image receptor. Based on the number of photons collected in a predefined region of the detector the scan velocity is modified. This region is referred to as the feedback region. The idea is that, if the count rate in the feedback region is changing so should the scan-speed in order to control the number of counts reached per x-dimension pixel. This method includes feedback from the actual image receptor based on the count rate in the feedback region. This feedback is in near real time and will control the scan speed of the detector. The effect will be that the exposure of each point along the x-axis will be controlled based on the count rate of the feedback region and thus the entire image will have a controllable signal level along the x-dimension at least in the feedback region in the y-dimension. Another effect is that the total scan time will be minimized since areas not covered by dense objects will be scanned faster and thus exposed shorter.

The exposure control according to the present invention uses the detector itself to control the exposure. In the scanning system the exposure time is function of the scan-velocity. This allows controlling the exposure time by controlling the scan-velocity based on the signals received from the detector array.

Figure 3:
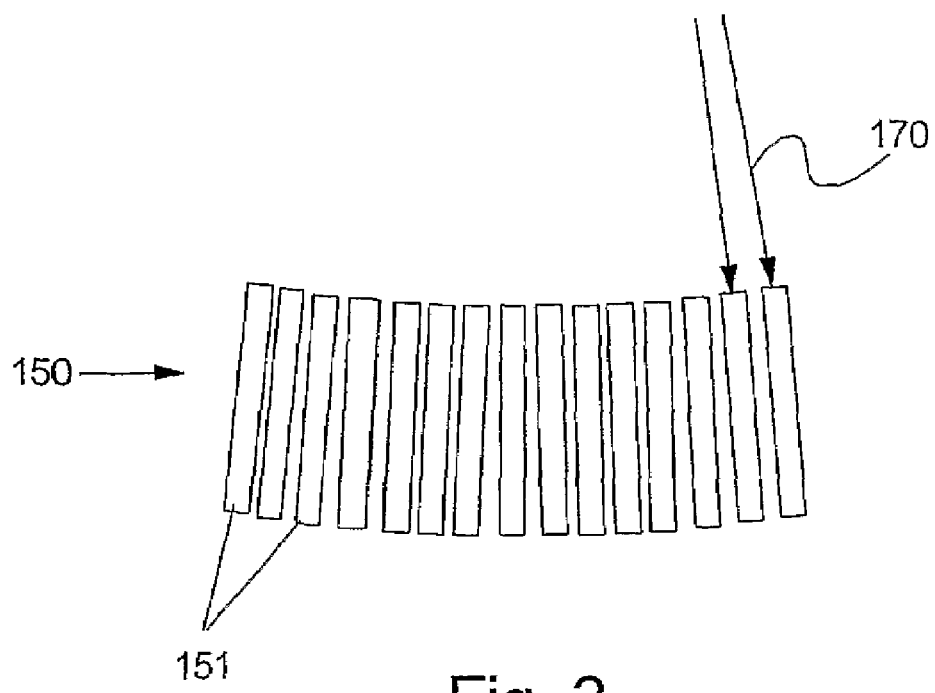
FIG. 3 illustrates in a schematic way a part of a detector assembly.

FIG. 3 illustrates a detector array 150 comprising a number of lined up sensors 151. Each sensor constitutes a pixel. The invention can be implemented by allowing a section of the detector array, e.g. the sensors on the edge of the detector corresponding to the scanning direction, i.e. scanning the object first determines the scan-speed and thus exposure time. Reference numeral 170 denotes x-rays. Consequently, in the scanning system the exposure time of each pixel can be controlled.

According to one preferred embodiment, the control method comprises the steps of (flow diagram of FIG. 4):

Setting target signal 400, e.g. number of photons counted or SNR (in this square rot of number of photons)

Setting a detector Region Of Interest (ROI), 401

Setting a start velocity, 402

Start scanning, 403

Collecting a signal from ROI, 404

Compensating the signal with respect to ROI size and efficiency, 405

Comparing the signal with target signal ($S_{target}$) and calculate new optimal velocity, 406. In the case of a photon counting device the new velocity $V_{new}$ may be calculated as $V_{new}=V_{old} \times S_{target}/S_{measured}$ Setting a new velocity, 407

Next readout.

Wherein the step of comparing the signals may comprise, FIG. 5:

If target signal is higher than measured signal, 406', then decrease velocity 4061', else keep old velocity 4062'.

This is due the fact that a control with respect to the densest area in the breast is desired. This is applicable in the case in which the ROI width is less than the entire detector width.

The step of comparing signals may also include setting a minimum velocity.

The control method may increase velocity, instead of keeping old velocity, in the case when the target signal is lower than the measured signal. A conventional controller whose parameters are chosen to take detector design into consideration may implement the control of the velocity. E.g. a narrow detector may use a control algorithm with a more rapid response than a wider one.

Another alternative comparing signal step may also be (FIG. 7):

If target signal is higher than measured signal 406''', then decrease velocity 4061''', else Collect compression height ($h_{compression}$) data, collect projection from the stand control unit and collect data about examination type (phantom, implant, specimen etc), 4062''', Based on above, estimate typical breast density profile from previous examinations, 4063'''

Based on estimated density profile and measured signals (i.e. measured actual density profile) calculate optimal velocity profile for remaining, 4064''', The target signal can be calculated from object thickness and spectrum incident on the object.

The data about the examined object is obtained from a database including previous examinations, estimations, etc.

The step of choosing the ROI may include:

Decide scan direction,

Chose ROI that will enter breast first, and

Check that ROI has sufficiently number of detector elements working else chose next appropriate ROI.

FIG. 8 illustrates the arrangement of the invention in conjunction with the X-ray apparatus of FIG. 2. The object (e.g. breast) 160 to be examined is positioned between the collimator 140 and the detector assembly 150 in the path of x-rays 170. The signal from the detector is read out by a readout unit 801 and provided to a processing unit 802 (modality unit computer), based on output from which a motor controller 803 controls the motor 804 driving the X-ray imaging part of the apparatus in a semi-rotational motion.

The signal is collected every time the detector has travelled a pre-set value. In this case it will be equal to the pixel width of the acquired image. The pixel data is normalized with the time elapsed since last readout. However, the signal to the AEC is not normalized. These results in an image quality independent of scan velocity. The system can modify the scan speed throughout the scan and allow different parts of the image to have different exposure time, depending on the depicted object.

It is also possible to use a part of the detector array to control the scan-speed. If the signal or calculation rate in that part is changing so should the scan speed in order to control the level of statistics in the image. The feedback from the detector array to the scan speed can be made substantially in real time.

One effect of the proposed exposure control is that the total scan time will be reduced since areas not covered by dense objects will be scanned faster.

The invention is not limited to the shown embodiments but can be varied in a number of ways without departing from the scope of the appended claims and the arrangement and the method can be implemented in various ways depending on application, functional units, needs and requirements etc.

The invention claimed is:

1. A method of real-time controlling exposure time in an x-ray apparatus, the apparatus comprising an x-ray source and a displaceable detector arranged to move with a controllable speed across an image exposure area, said detector having a first and a second edge, said first edge being adjacent to a movement direction of said detector, the method comprising the steps of:
  a. setting a target signal, calculated to obtain a pre-defined signal to noise ratio (SNR),
  b. setting a detector Region Of Interest (ROI), comprising a sensor in said first edge,
  c. start scanning,
  d. collecting a signal from said ROI (404),
  e. compensating the signal with respect to at least one of ROI size and efficiency,
  f. comparing the signal with a target signal ($S_{target}$) and calculating a new optimal velocity (406), and
  g. setting a new velocity during said scanning.

2. The method of claim 1, wherein the target value is calculated from a thickness of the object to be inspected and spectrum incident on the object.

3. The method of claim 1, wherein the signal is acquired from a discrete number of regions on said detector.

4. The method of claim 1, wherein the detector is a photon-counting detector and the signal is the counted number of photons.

5. The method of claim 1, wherein a distance the detector moves between readouts defines pixels in the scan direction as a first dimension, and in a second dimension, the detector comprises actual pixels.

6. The method of claim 1, wherein the detector functions as a part of an exposure control system and an image receptor.

7. The method of claim 1, wherein based on a number of photons collected in a predefined region of the detector, the scan velocity is alternated.

8. The method of claim 7, further comprising changing scan-speed with respect to a count rate change in said region for controlling the number of counts reached per a first dimension pixel.

9. The method of claim 7, comprising a feedback from said displaceable detector based on the count rate in said region.

10. The method of claim 9, wherein said feedback is real-time and controls the scan speed of the detector.

11. The method of claim 10, wherein the exposure of each point along an x-axis is controlled based on the count rate of said region and thus the entire image has a controllable signal level along the first dimension at least in said region in the second dimension.

12. The method of claim 9, further comprising the step of minimizing total scan time by areas not covered by dense objects being scanned with increased speed and thus exposed shorter.

13. The method of claim 1, wherein said detector itself is used to control the exposure.

14. The method of claim 1, wherein said step d comprises reading a number of counted photons or SNR.

15. The method of claim 1, wherein said x-ray apparatus is a photon counting device and a new velocity ($V_{new}$) is calculated as $V_{new} = V_{old} \times S_{target}/S_{measured}$, wherein $V_{old}$ is the old velocity, $S_{target}$ is target signal and $S_{measured}$ is a measured signal.

16. The method of claim 1, wherein in said step f, if target signal is higher than measured signal then the velocity is decreased otherwise old velocity is maintained.

17. The method of claim 1, wherein said step f includes requiring new velocity to be at least higher than a pre-set minimum velocity.

18. The method of claim 1, wherein depending on detector size the velocity decreases, if the target signal is higher than the measured signal otherwise the velocity is increased.

19. The method of claim 1, comprising the alternative step f, said alternative step comprising:
  a. collecting a compression height ($h_{compression}$) data, projection and data about an examination type,
  b. collecting from previous examinations, based on previous step, typical examination object density profile,
  c. calculating an optimal velocity profile based on estimation of said density profile and measured signals, and
  d. calculating new velocity based on data from steps a.-c.

20. The method of claim 1, wherein said step of choosing the ROI includes:
  a. deciding an scan direction,
  b. choosing an ROI that will enter the object first, and
  c. checking that said ROI has a sufficient number of operative detector elements working else choosing next appropriate ROI.

21. An arrangement for controlling exposure time mountable in an x-ray apparatus comprising an x-ray source and a displaceable detector arranged to be displaced with a controllable speed across an image exposure area, and said detector having a first edge arranged as leading edge in a displacement direction, said detector further comprising a Region Of Interest (ROI) comprising a sensor in said first edge, the arrangement comprising arrangement for setting a target signal, calculated to obtain a pre-defined signal to noise ratio (SNR), arrangement for obtaining a start velocity, arrangement for collecting a signal from said ROI, arrangement for compensating the signal with respect to at least one of ROI size and efficiency, comparing arrangement for comparing the signal with a target signal ($S_{target}$), arrangement for calculating a new optimal velocity, and an arrangement for setting a new velocity during said scanning.

22. The arrangement of claim 21, wherein said arrangement for receiving detected signals is a processing unit and said arrangement (804) for controlling the detector replacement is a motor controller.

23. The arrangement of claim 21, wherein said displacement controller controls rotation of said detector having a rotation centre in said x-ray source.

24. An X-ray apparatus of a photon counting type, said apparatus comprising an x-ray source and a displaceable detector being configured to move with a controllable speed across an image exposure area, in a direction, said apparatus further comprising:
  a. an arrangement configured to count a number of photons detected by said displaceable detector, which comprises an end portion arranged as a leading edge in said direction,
  b. a comparator arrangement configured to compare the counted number of photons from a sensor in said end portion under a scanning movement with a pre-set value, and
  c. a controller arrangement configured to:
    i. set a target signal, calculated to obtain a pre-defined signal to noise ratio (SNR),
    ii. set a detector Region Of Interest (ROI), comprising a sensor in said leading edge,
    iii. collect a signal from said ROI, and compensate said signal with respect to at least one of ROI size and efficiency,
    iv compare said signal with a target signal ($S_{target}$) and calculating a new optimal velocity; and,
    v. set a new velocity during said scanning.

* * * * *

UNITED STATES PATENT AND TRADEMARK OFFICE
CERTIFICATE OF CORRECTION

PATENT NO. : 7,496,176 B2  
APPLICATION NO. : 10/597965  
DATED : February 24, 2009  
INVENTOR(S) : Magnus Aslund Page 1 of 1

It is certified that error appears in the above-identified patent and that said Letters Patent is hereby corrected as shown below:

On the Title page:

Item 73: DELETE "Sectra Mamea, Kista (SE)" and

INSERT, therefor:

-- Sectra Mamea AB, Kista (SE) --

Signed and Sealed this

Ninth Day of June, 2009

JOHN DOLL  
*Acting Director of the United States Patent and Trademark Office*